(12) United States Patent
Kauffman et al.

(10) Patent No.: US 7,371,534 B2
(45) Date of Patent: May 13, 2008

(54) SENSITIVE INTRACELLULAR CALCIUM ASSAY

(75) Inventors: Linda Kauffman, San Carlos, CA (US); Rajendra Singh, San Jose, CA (US); Edwin F. Ullman, Atherton, CA (US)

(73) Assignee: Discoverx Corporation, Fremont, CA (US)

( * ) Notice: Subject to any disclaimer, the term of this patent is extended or adjusted under 35 U.S.C. 154(b) by 365 days.

(21) Appl. No.: 11/135,779

(22) Filed: May 23, 2005

(65) Prior Publication Data

US 2006/0003388 A1    Jan. 5, 2006

Related U.S. Application Data

(60) Provisional application No. 60/574,062, filed on May 25, 2004.

(51) Int. Cl.
  *G01N 33/53* (2006.01)
  *A61K 51/00* (2006.01)
(52) U.S. Cl. .............. 435/7.1; 435/7.92; 436/501; 436/518; 422/61; 424/1.49; 424/178.1; 424/184.1
(58) Field of Classification Search ............ 435/7.1, 435/7.92; 436/501, 518; 422/61; 424/178.1, 424/184.1, 1.49
  See application file for complete search history.

(56) References Cited

U.S. PATENT DOCUMENTS

| | | | |
|---|---|---|---|
| 4,444,879 A | * | 4/1984 | Foster et al. ............... 435/7.95 |
| 4,532,203 A | * | 7/1985 | Ullman et al. ............. 435/7.24 |
| 6,221,612 B1 | | 4/2001 | Knapp et al. |
| 6,420,183 B1 | | 7/2002 | Krahn et al. |

FOREIGN PATENT DOCUMENTS

NL        7706351    * 12/1978

OTHER PUBLICATIONS

Edelman et al. (Cell Calcium, 1994, vol. 16, No. 3, pp. 181-183) Abstract Only.*
Philipp et al. (The EMBO Journal, vol. 17, No. 15, 1998, pp. 4274-4282).*
Larry A. Sklar, et al., "Ligand/receptor internalization: a spectroscopic analysis and a comparison of ligand binding, cellular response, and internalization by human neutrophils," *J. of Cell Biochemistry*, 1982, vol. 20, No. 2 193-202.
Jos Van Renswoude, et al., "Receptor-mediated endocytosis of transferrin and the uptake of Fe in K562 cells: Identification of a nonlysosomal acidic compartment," *Proc. Natl. Acad. Sci. USA*, Oct. 1982, vol. 79, 6186-6190.
J. M. Schober, et al., "Effect of cellular and receptor activation on the extent of integrin $\alpha_{IIb}\beta_3$ internalization," *Journal of Thrombosis and Haemostasis*, Nov. 2003, vol. 1, 2404-2410.
Paul P. M. Schnetkamp, et al., "Regulation of Free Cytosolic $Ca^{2+}$ Concentration in the Outer Segments of Bovine Retinal Rods of Na-Ca-K Exchange Measured with Fluo-3," *Journal of Biological Chemistry*, Dec. 5, 1991, vol. 266, No. 34, 22975-22982.

* cited by examiner

*Primary Examiner*—Long V. Le
*Assistant Examiner*—Lisa V Cook

(57) ABSTRACT

A sensitive intracellular calcium assay is disclosed comprising conveniently a reagent comprised of a dye precursor capable of entering cells and being hydrolyzed to a dye, whereby the dye complexes with calcium in the cells and provides a luminescent signal, an antibody specific for the dye and conjugated with a quencher, and a cellular anion exchange enzyme inhibitor. In performing the assay, the reagent is combined with cells expressing a receptor responsive to a ligand resulting in a change in cytosolic calcium. After incubation for the dye precursor to permeate the cells, the calcium may be determined by exciting the dye precursor and determining the peak fluorescence over a time course. The method can be used for measuring the effect of an agent on cytosolic calcium by binding to a cell surface membrane receptor.

9 Claims, 1 Drawing Sheet

SENSITIVE INTRACELLULAR CALCIUM ASSAY

CROSS-REFERENCE TO RELATED APPLICATIONS

This application claims priority from U.S. Provisional Patent Application No. 60/574,062 filed on May 25, 2004, which is hereby incorporated by reference in its entirety.

BACKGROUND OF THE INVENTION

1. Field of the Invention

The field of this invention is the determination of intracellular calcium.

2. Related Art

The discovery that calcium plays a pleiotropic role in regulating cells in their response to ligands created an interest in being able to detect the level of calcium in cells in response to various agents, e.g. ligands, agonists and antagonists. Calcium plays a critical role in neuronal cells, muscle cells and other cells, where the cytosolic calcium acts as a regulator of cell expression. Because calcium is used by so many receptors and ion channels as a regulator of pathways leading to cellular function, measuring calcium can be a vicarious measure of the activity of a drug in regulating an ion channel or a receptor. Toward being able to measure cytosolic calcium, dyes have been developed that can enter a cell and fluoresce when bound to calcium. Measurement of the intracellular fluorescence provides a measure of the cytosolic calcium and, perforce, the activity of a compound in relation to a particular receptor. One can ensure that the target receptor is being measured, by using a competition between a known antagonist or introducing a gene(s) encoding a receptor or ion channel into a cell that would otherwise not respond to a drug by inducing a change in calcium concentration in the cytosol.

One problem in fluorescence measurement in biomedical assays is often that the fluorescence changes correlated with the biological cell action are small compared with the non-specific background fluorescence. As a result, the resolving power is greatly restricted. Conventional commercial measuring systems (fluorescence readers, Dynatech or SLT), cannot solve the problem, because owing to their optical measuring arrangement (excitation from 'above' through the fluorescent liquid column of the supernatant) the signal can barely be detected in comparison with the background.

Even very complicated measuring systems (NovelTech, FLIPR: Fluorescence Imaging Plate Reader) are only able to decrease this background fluorescence using a special laser illumination geometry (excitation below about 45°). Therefore, trying to solve the problem of background fluorescence by sophisticated instrumentation has not been entirely satisfactory.

In many cases of receptor or ion channel binding studies using fluorescently or luminescently labelled ligands, the labelled and unbound fraction in each case is removed by processes like washing. The washings introduce many uncertainties in the results, since cells can be subject to lysis, bound labeled ligand may be released, and unbound labeled ligand may be inadequately removed. There is, therefore, a need for a sensitive reliable methodology for measuring calcium without the introduction of methodologies that introduce uncertainties and variabilities in the results.

The subject invention provides improved sensitivity of optical analysis of fluorescently labeled or luminescent cells in a cellular assay in order to be able to measure, for example, membrane potential changes which are as low as possible on the basis of fluorescence changes of potential-sensitive dyes. In this case, the sensitivity of the measuring system should be sufficient that potential changes of below 5 mV can be detected at least qualitatively. In the case of luminescent cells, an increase in the detection of the luminescence signal should be achieved. Moreover, the method should be suitable for screening with a high sample throughput.

Relevant Literature

U.S. Pat. Nos. 6,420,183 and 6,221,612 describe cellular assays and methods for reducing background. Antibodies have been used in the past to quench fluorescent dyes that are spilled from cells upon cell lysis or other breaching of the cell membrane (U.S. Pat. No. 4,532,203). They have also been used to differentiate extracellular from internalized fluorescein labeled proteins (Sklar LA., J Cell Biochem 1982;20(2): 193-202; van Renswoude J, Proc Natl Acad Sci USA 1982 Oct;79(20):6186-90; and Schober JM, J Thromb Haemost. 2003 Nov;1(11):2404-10). Schnetcamp, et al. (1991) J. of Biol. Chem. 266, 22975-82 reports the use of antibodies in a calcium assay to remove background signal.

BRIEF SUMMARY OF THE INVENTION

Intracellular calcium is measured in intact cells by employing a reagent comprising a fluorescent or luminescent dye precursor for calcium and quencher conjugated antibodies, where the antibodies bind specifically to the extracellular luminescent dye. The reagent is added to host cells and incubated, followed by addition of the agent that affects cytosolic calcium concentration and without a wash, the luminescence read over a time span.

DESCRIPTION OF THE SPECIFIC EMBODIMENTS

Figure 1:
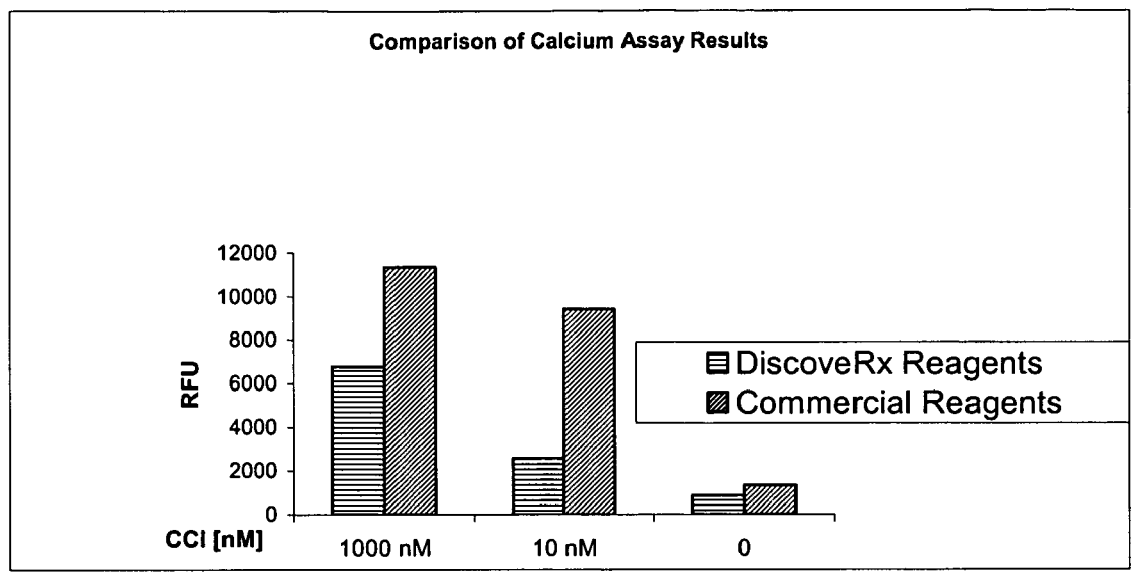
FIG. 1 is a bar graph showing a comparison of calcium assay results when using prior art and the present reagents.

In accordance with the subject invention, intracellular, normally cytosolic, calcium concentrations are measured in host cells, normally in response to a stimulus in the environment. The method employs as a reagent a combination of a luminescent precursor and an antibody specific for the luminescent dye, where the antibody is conjugated with a quencher for quenching the luminescence of the dye to which the antibody is bound. The reading employing excitation light can be performed through the vessel. The protocol is simplified by adding a single reagent to the cells for introducing the dye precursor into the cells, inhibiting transport of hydrolyzed luminescent dye from the cells and scavenging any extracellular formation of the luminescent dye without having to remove the excess dye precursor present in the extracellular medium. A time scan of the change in signal is made to identify the peak signal.

The dye precursor is characterized by not being luminescent under the conditions of the assay, being an ester capable of being hydrolyzed intracellularly to the luminescent oxy compound, and providing enhanced luminescence upon complexing with calcium. The esters are chosen to be susceptible to hydrolysis by intracellular hydrolases. A number of commercially available dyes fulfilling the above requirements are known. Fluorescent dyes for monitoring Ca++ are well known and described in detail in section 20.1-20.4 of the Molecular Probes catalog, 9th edition. They usually have two bis-carboxymethylamino groups attached to a fluorescent nucleus such as fluoresceins, rhodamines, coumarins, aminophenylindoles, and others. For the most part the compounds are 3,6-dioxy substituted xanthenes, where in the precursor the oxy groups are substituted and in the luminescent dye they are unsubstituted. Usually there are acetoxymethyl groups protecting the phenols and acids. See, for example, Fluo¾, Fura⅔, calcein green, etc. Hydrolysis of the acetyl group results in the luminescent product. The precursors are able to cross the cellular membrane and be hydrolyzed in the cell. Unfortunately, some of the precursor is hydrolyzed extracellularly and reacts with calcium in the supernatant to produce luminescence during the measurement of intracellular dye. This background greatly impedes accurate measurement of the intracellular calcium complexed with the intracellular dye.

In conjunction with the dye precursor, quencher conjugated antibody is added as a composite reagent. While the antibody can be added in a separate step, either before or after addition of the dye precursor, for convenience, the two are combined in a single reagent. In this way, in case of adventitious hydrolysis of the dye precursor, such hydrolysis product will react with the antibody prior to addition to the cells. Furthermore, since the antibody is found not to interfere with the entry of the dye precursor into the cells, the user need only add the single reagent to obtain the result avoiding measuring of volumes and is ensured of the proper ratio of the two components of the reagent. Also added is an inhibitor of cellular anion exchange enzyme in order to prevent the leakage or transport of the anionic luminescent dye from the cells.

The assay is performed simply by growing the host cells in an appropriate container. The host cells may be any vertebrate cells that have the appropriate receptor or ion channel (collectively "cell membrane protein receptor") and provides for a change in the intracellular calcium detected by the dye upon binding to a ligand. The cell may be a naturally occurring cell, native cells, a cell line, tissue culture, genetically modified cell, etc. so long as the cell is able to be maintained during the assay, desirably growing in a culture medium, and has the appropriate cell membrane protein receptor(s) and responds to binding of a ligand to the cell membrane protein receptor(s) by changing the calcium in the cytosol available for binding to the dye. The cells will usually be mammalian cells, such as human cells, mouse cells, rat cells, Chinese hamster cells, etc. Cells of particular interest include neuronal cells, ganglions, muscle cells, glial cells, myocytes, etc. Alternatively, one may use cell lines that are readily grown in culture and have been modified with the appropriate cell membrane protein receptor(s). Cells that are found to be convenient include CHO cells, HeLa cells, HEKs, etc.

Conveniently, cells may be seeded in an appropriate container, e.g. microtiter well, and expanded over about 6 to 48 h in a culture medium. Generally about $10^3$ to about $10^6$ cells will suffice. After the cells have grown to the desired number, generally to confluence, the culture medium is replaced with the assay medium. At this time an inhibitor of a cellular anion exchange enzyme may be added to diminish interference with the calcium measurement that should be solely related to the binding of the ligand. Conveniently probenecid may be used as such an enzyme inhibitor (inhibiting a plasma membrane ATPase), at a concentration of 0.5 to 5 mM, although other inhibitors such as sulfinpyrazones and disulfonated stilbenes are also conventionally employed. The probenecid is present in the dye loading buffer typically at 1-2.5 mM in the homogeneous assay format, and is added to reduce leakage of the deesterified indicator dye. As indicated previously, there are two primary reagents: the dye precursor; and antibody specific for the dye (hydrolyzed dye precursor) conjugated to a quencher. The amount of dye that is employed is not critical to the invention, but needs to be sufficient to provide the necessary intracellular concentration for detecting calcium. Generally the concentration of the dye will be in the range of 0.5 to 10 µM, more usually in the range of about 1 to 5 µM for the range of the number of cells indicated above. The amount of antibody will generally be in the range of about 50 to 500 nM, more usually in the range of about 100 to 300 nM. The antibody will be conjugated to a quencher for the dye that is employed. There are a number of excellent commercially available quenchers that can be conjugated to the antibodies that can be used regardless of whether there is intrinsic quenching. p-Aminophenylazo compounds such as Dabcyl (dimethylaminophenylazobenzoic acid) and BHQ (Black Hole Quencher) which is a bis-azobenzene derivative, are frequently used. 4,5-dimethoxyfluorescein and its derivatives are particularly useful quenchers of fluoresceins. Usually 2-15 molecules of the quenchers will be bound to an antibody. More quencher makes quenching more efficient but can destabilize or cause precipitation of the antibody, so there is a trade off which is best addressed experimentally for each antibody. When larger numbers of quencher dyes are used they can be attached to a polymer such as dextran to which the antibody will also be bound. This will both improve solubility and reduce the adverse effects on the antibody. The antibodies can also be attached to particles that serve as quenchers, particularly colloidal carbon, silver, gold and insoluble dye crystallites are useful.

The method of conjugation is conventional and commercially available reagents can be used. Conveniently, there are monoclonal antibodies to fluorescein that do not bind significantly to the ester precursor of fluorescein, so that the loss of dye and antibody is minimized.

The assay volume will generally be in the range of about 10 to 500 µl, more usually in the range of about 20 to 100 µl. The reagent solution will usually be buffered with a conventional buffer, such as HEPES, MOPS and PBS, generally at a concentration in the range of about 50 to 250 nM and at a pH in the range of about 7-7.5. Small amounts of other additives may be employed, such as non-ionic detergents, e.g. Pluronics, at a concentration in the range of about 0.05 to 0.25% and a protein that is non-interfering, e.g. bovine serum albumin, in an amount in the range of about 0.5 to 2%. These additives serve to reduce non-specific binding, prevent components from sticking to reaction vessel and disperse the hydrophobic indicator dye in an aqueous medium The cells and reagent solution are incubated for sufficient time for the dye precursor to enter the cells in a sufficient amount to allow for detection of the available calcium in the cell. Generally, the time for the incubation will be in the range of about 0.5 to 3 h, the time being a matter of convenience, so long as the desired dye concentration in the cells is achieved and the cells are not adversely affected by the extended time. At this time the agent of interest is added, generally in a volume of about 10 to 50 µl and luminescence reading can begin in a matter of seconds, where peak luminescence is read. Commercially available devices read luminescence, fluorescence and chemiluminescence, and monitor the readings for the peak. The peak result is recorded and, as appropriate, the time to the peak result.

The time scan will usually be at least about 0.5 min and not more than about 30 min, usually not more than about 15 min. The assay can be read with the excitation light passed through the sample or using a reflectometer or by total internal reflection. Since substantially any dye that forms outside of the cells in the supernatant will be quenched, the signal from the supernatant does not interfere with the signal from the cells.

Cell membrane protein receptors of interest include the muscarinic receptors, GPC receptors, sodium, potassium and calcium channels, chloride channels, and other receptors. By employing cells having one or more of these cell membrane protein receptors, where the binding to the receptor results in a change in the calcium in the cytosol, one can rapidly screen compounds for their effect on the calcium level in the cell and their ability to bind to the cell membrane protein receptor and activate the receptor. Alternatively, if one is interested in an antagonist, one can employ the candidate compound with a known agonist and determine the effect of the candidate compound on the activity of the known agonist.

The subject assay provides for a large dynamic range providing for at least about a 100% increase going from 10 nM carbachol to 1000 nM carbachol as the stimulating agent. Therefore, the value at 1000 nM is at least twice the value at 10 nM or greater.

The subject methodology lends itself to high throughput screening, employing a single reagent and conventional procedures and equipment. The assay provides a broad dynamic range so that the activity of a compound can be readily determined. As compared to a commercially available assay, the subject assay provides for a much greater differential between two concentrations than the alternative assay.

For convenience, the reagent and other components of the assay may be provided in kits, where the reagent (dye precursor and quencher conjugated antibody) may be present as a reconstitutable powder or as a cooled solution or ice, in a buffer. The kit may also include buffer, inhibitor of cellular anion exchange enzyme(s), non-interfering protein, which may be separate or present in the buffer, non-ionic detergent, also separate or in the buffer, host cells, etc. Of particular interest are host cells that are not neuronal cells, but have been genetically engineered to produce a neuronal cell surface membrane receptor. The amounts of the various components would be interrelated in relation to their use in the assay.

The following examples are offered by way of illustration and not by way of limitation.

EXPERIMENTAL

Example 1

Conjugation of Anti-Fluorescein with Dabcyl Succinimidyl Ester

A 10 mg/ml solution of the labeling reagent in DMSO was freshly prepared. A protein solution (monoclonal antibody from Molecular Probes or Chemicon) at 1 mg/ml in phosphate buffer ($NaH_2PO_4$, 20 mM, pH 7.4) was treated with 20 µl of the labeling reagent (Dabcyl succinimidyl ester from Molecular Probes, Eugene Oreg.). The reaction mixture was incubated at room temperature in an end over end shaker for 1 hour. The reaction mixture was quenched with 100 µl of 0.2M $Na_2CO_3$ solution and transferred to a microdialysis cassette with a molecular weight cutoff of 10 kD (Pierce, Milwaukee). Dialysis into phosphate buffered saline with three changes at 4 hr intervals was performed. A total of 1 ml reaction volume was dialyzed against 3×1 L. The dialysed antibody conjugate was analysed by UV-Vis spectrometry to determine dye loading efficiency. Typically the degree of loading was 2-5 quencher molecules per antibody. Antibody concentration was determined from absorbance at 280 nm with a correction factor of 0.4 for the dye. The absorbance at 280 nm of a 1 mg/ml solution of an antibody is 1.4. The concentration of the dye was determined from its extinction coefficient ($32000 M^{-1} cm^{-1}$) at 454 nm.

Example 2

Assay for the Effect of Carbachol, a Muscarinic Receptor Agonist

Method:

Assay is run in a standard 384-well microtiter plate with a clear bottom. Cells are seeded at a density of 30,000 cells/well, and allowed to grow overnight in standard tissue culture medium, under standard tissue culture conditions.

The next day, tissue culture supernatant is removed, and 50 µl of Calcium Reagent (Molecular Devices, Sunnyvale Calif.) is added to the wells. Plate is incubated for 1 hour at 37EC in a standard tissue culture incubator. This step loads the dye into the cells.

After the 1 hour incubation, the plate is transferred to the Molecular Device FLIPR instrument, which measures the cellular fluorescence (excitation at 488 nm /emission 515 nm filter), in one second intervals. The dye is hydrolyzed in the cell by esterases and becomes fluorescent. The instrument adds 25 microliters of carbachol (agonist for cellular calcium response) 10 seconds after the initiation of the read, and the increase in free cellular calcium resulting from carbachol stimulation is measured as an increase in cellular fluorescent signal.

The reagent: 3 µM Fluo-4 AM dye (Molecular Probes, Eugene Oreg.), 150 nM antibody in HEPES buffer (pH 7.4) containing 1% fetal bovine serum (Sigma), 0.1% Pluronic F127 (BASF) and 0.5 mM probenecid (Sigma) is added.

Instrument software identifies peak fluorescence, which is directly correlated to cellular calcium levels.

| Calcium Assay, RFU | | |
|---|---|---|
| Carbachol concentration | DiscoveRx Reagents | Commercial Reagents |
| 1000 nM | 6767 | 11348 |
| 10 nM | 2589 | 9410 |
| 0 | 874 | 1334 |

The data from the above table are also presented as FIG. 1. There, the legends "DiscoveRx Reagents" and "Commercial Reagents" refer respectively to the present reagents and prior art reagents, namely Quencher-Ab conjugate + and −.

It is evident from the above results that the subject reagents provide for a much larger dynamic range. The change in signal for the present reagents in going from 10 nM to 1000 nM is 4178 RFU (relative-fluorescence units), a change of 161 percent based on the value at 10 nM, while the difference for the commercial reagent is 1938, a change of only 21 percent. This indicates that it would be difficult with the commercial reagent to distinguish between intermediate concentrations. The subject assay provides for a substantial improvement over existing methods for evaluating agents for their effect on cytosolic calcium and adds an important addition in drug discovery and analysis of cellular pathways. Surprisingly, the reagents do not react with each other. While the antibody is directed to the dye, not the ester, the dye precursor is in an extraordinarily larger amount than any extracellular dye, so that even a low binding constant with the dye precursor could have resulted in an extensive reaction between the dye precursor and the antibody.

All references referred to in the text are incorporated herein by reference as if fully set forth herein. All procedures disclosed in the references are incorporated as demonstrating the level of skill in the art to perform the procedures indicated in this application. The relevant portions associated with this document will be evident to those of skill in the art. Any discrepancies between this application and such reference will be resolved in favor of the view set forth in this application.

Although the invention has been described with reference to the above examples, it will be understood that modifications and variations are encompassed within the spirit and scope of the invention. Accordingly, the invention is limited only by the following claims.

What is claimed is:

1. A method for determining intracellular calcium comprising:
    adding to cells a dye precursor capable of entering the cells and being hydrolyzed to a dye, whereby the dye complexes with calcium in said cells and provides a luminescent signal, an antibody specific for the dye and not the dye precursor, said antibody conjugated with a quencher for quenching extracellular hydrolyzed dye precursor, said quencher being a p-aminophenylazo compound or a 4,5-dimethoxyfluorescein, and a cellular anion exchange enzyme inhibitor for inhibiting cell entry of extracellular calcium;
    incubating for sufficient time for said dye precursor to enter said cells; and determining in the presence of said dye precursor over a time span the change in the luminescent signal from said dye with decreased extracellular dye signal as a measure of intracellular calcium.

2. A method according to claim 1, wherein said luminescent signal is fluorescence and said determining comprises illuminating said cells with excitation light.

3. A method according to claim 1, wherein said dye precursor is a xanthene ester and said antibody is a monoclonal antibody specific for the hydrolyzed xanthene ester.

4. A method according to claim 1, wherein said dye is selected from the group consisting of Fluo¾, Fura⅔, and calcein green.

5. A method according to claim 1, wherein the signal is at least about twice the signal at 1000 nM carbachol as the signal at 10 nM carbachol.

6. A method according to claim 1, wherein said quencher conjugated antibody has on the average from about 2 to 15 quencher molecules per antibody.

7. A method according to claim 1, further comprising an agent wherein said agent binds to a neuronal receptor.

8. A method according to claim 1, further comprising an agent wherein said agent binds to an ion channel.

9. A method according to claim 1, wherein said cells are genetically modified to express a cell surface membrane receptor.

* * * * *

UNITED STATES PATENT AND TRADEMARK OFFICE
CERTIFICATE OF CORRECTION

| | |
|---|---|
| PATENT NO. | : 7,371,534 B2 |
| APPLICATION NO. | : 11/135779 |
| DATED | : May 13, 2008 |
| INVENTOR(S) | : Linda Kauffman et al. |

Page 1 of 1

It is certified that error appears in the above-identified patent and that said Letters Patent is hereby corrected as shown below:

<u>Column 8</u>

Line 17, delete "Fluo¾, Fura⅔" and insert --Fluo3/4, Fura2/3-- after: of

Signed and Sealed this

Twenty-ninth Day of July, 2008

JON W. DUDAS
*Director of the United States Patent and Trademark Office*